United States Patent
Ward et al.

(10) Patent No.: US 11,484,217 B2
(45) Date of Patent: Nov. 1, 2022

(54) OCULAR IMPEDANCE-BASED SYSTEM FOR BRAIN HEALTH MONITORING

(71) Applicant: THE REGENTS OF THE UNIVERSITY OF MICHIGAN, Ann Arbor, MI (US)

(72) Inventors: Kevin Ward, Superior Township, MI (US); Mohamad Hakam Tiba, Ann Arbor, MI (US); Ashwin Belle, Ann Arbor, MI (US); Sardar Ansari, Richmond, VA (US); Parag G. Patil, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 165 days.

(21) Appl. No.: 16/613,707

(22) PCT Filed: May 16, 2018

(86) PCT No.: PCT/US2018/032984
§ 371 (c)(1),
(2) Date: Nov. 14, 2019

(87) PCT Pub. No.: WO2018/213456
PCT Pub. Date: Nov. 22, 2018

(65) Prior Publication Data
US 2021/0169362 A1   Jun. 10, 2021

Related U.S. Application Data

(60) Provisional application No. 62/506,971, filed on May 16, 2017.

(51) Int. Cl.
*A61B 5/053*   (2021.01)
*A61B 5/026*   (2006.01)
(Continued)

(52) U.S. Cl.
CPC .............. *A61B 5/053* (2013.01); *A61B 5/026* (2013.01); *A61B 5/031* (2013.01); *A61B 5/0816* (2013.01);
(Continued)

(58) Field of Classification Search
CPC ......... A61B 5/026; A61B 5/031; A61B 5/053; A61B 5/4064
See application file for complete search history.

(56) References Cited

U.S. PATENT DOCUMENTS 4,771,784 A   9/1988   Kozin et al.
5,068,619 A   11/1991   Nakano et al.
(Continued)

FOREIGN PATENT DOCUMENTS

WO   WO-93/20499 A1   10/1993

OTHER PUBLICATIONS

Tiba et al., Novel noninvasive method of cerebrovascular blood volume assessment using brain bioimpedance, J. Neurotrauma, 34:3089-96 (Nov. 15, 2017).
(Continued)

*Primary Examiner* — Daniel L Cerioni
*Assistant Examiner* — Raymond P Dulman
(74) *Attorney, Agent, or Firm* — Marshall, Gerstein & Borun LLP

(57) ABSTRACT

Methods and systems monitor and assess brain bioimpedance through the use of an ocular window that assesses dynamic changes in cerebral blood volume (CBV). That ocular window is implemented through an ocular bioimpedance device that, in a non-invasive manner, measures numerous different brain health indicators using the bioimpedance measurements collected through the regions around the
(Continued)

eyes. The ocular bioimpedance device may be goggles with localized measurement electrodes that include cathodes and anodes.

6 Claims, 13 Drawing Sheets

(51) Int. Cl.
*A61B 5/03* (2006.01)
*A61B 5/08* (2006.01)
*A61B 5/00* (2006.01)

(52) U.S. Cl.
CPC .......... *A61B 5/4064* (2013.01); *A61B 5/4836* (2013.01); *A61B 5/6803* (2013.01)

(56) References Cited

U.S. PATENT DOCUMENTS

| | | | | |
|---|---|---|---|---|
| 5,726,916 A | * | 3/1998 | Smyth | A61B 5/398 702/151 |
| 8,172,769 B2 | | 5/2012 | Lenhardt et al. | |
| 2004/0176820 A1 | | 9/2004 | Paul | |
| 2005/0054939 A1 | | 3/2005 | Ben-Ari et al. | |
| 2006/0264775 A1 | | 11/2006 | Mills et al. | |
| 2007/0167694 A1 | * | 7/2007 | Causevic | A61B 5/318 600/301 |
| 2008/0200787 A1 | | 8/2008 | Shapira et al. | |
| 2010/0030054 A1 | | 2/2010 | Baruch et al. | |
| 2010/0189698 A1 | | 7/2010 | Willis | |
| 2010/0191140 A1 | * | 7/2010 | Terada | G06F 3/015 600/544 |
| 2011/0245734 A1 | | 10/2011 | Wagner et al. | |
| 2013/0190632 A1 | | 7/2013 | Baruch et al. | |
| 2014/0347265 A1 | * | 11/2014 | Aimone | H04W 4/029 345/156 |
| 2014/0358016 A1 | | 12/2014 | Shapira et al. | |
| 2014/0371545 A1 | | 12/2014 | Ben-Ari et al. | |
| 2015/0065813 A1 | * | 3/2015 | Wochlik | A61B 5/398 600/301 |
| 2016/0015289 A1 | * | 1/2016 | Simon | A61B 5/7275 600/301 |

OTHER PUBLICATIONS

European Patent Application No. 18801715.6, Extended European Search Report, dated Jan. 25, 2021.
Ang et al., "Temporal changes in cerebral tissue oxygenation with cerebrovascular pressure reactivity in severe traumatic brain injury.," J Neurol Neurosurg Psychiatry 78(3):298-302 (2007).
Antal et al., "Transcranial Alternating Current and Random Noise Stimulation: Possible Mechanisms," Neural Plast 2016:3616807, 12 pages (2016).
Baba et al., "Electrical stimulation of the cerebral cortex exerts antiapoptotic, angiogenic, and anti-inflammatory effects in ischemic stroke rats through phosphoinositide 3-kinase/Akt signaling pathway," Stroke 40(11):e598-605 (2009).
Babu et al., "Impedance plethysmography: basic principles," J Postgrad Med 36(2):57-63 (1990).
Bation et al., "Transcranial direct current stimulation in treatment-resistant obsessive-compulsive disorder: An open-label pilot study," Prog Neuropsychopharmacol Biol Psychiatry 65:153-157 (2016).
Berlim et al., "Clinical utility of transcranial direct current stimulation (tDCS) for treating major depression: a systematic review and meta-analysis of randomized, double-blind and sham-controlled trials," J Psychiatr Res 47(1):1-7 (2013).
Bhuta et al., "Technical aspects of impedance plethysmography," J Postgrad Med 36(2):64-70 (1990).
Buchman et al., "Precision Medicine for Critical Illness and Injury," Crit Care Med 44(9):1635-1638 (2016).
Budohoski et al., "The relationship between cerebral blood flow autoregulation and cerebrovascular pressure reactivity after traumatic brain injury," Neurosurgery 71(3):652-660 (2012).
Buitrago et al., "Effects of somatosensory electrical stimulation on neuronal injury after global hypoxia-ischemia," Exp Brain Res 158(3):336-344 (2004).
Czosnyka et al., "Continuous monitoring of cerebrovascular pressure-reactivity in head injury," Acta Neurochir Suppl 71:74-77 (1998).
Czosnyka et al., "Monitoring of cerebrovascular autoregulation: facts, myths, and missing links," Neurocrit Care 10(3):373-386 (2009).
Depreitere et al., "Pressure autoregulation monitoring and cerebral perfusion pressure target recommendation in patients with severe traumatic brain injury based on minute-by-minute monitoring data," J Neurosurg 120(6):1451-1457 (2014).
Faul et al., "Traumatic brain injury in the United States: emergency department visits, hospitalizations, and deaths 002-2006," in. Edited by Centers for Disease Control and Prevention, Control NCfIPa. Atlanta, GA, 1-74 (2010).
Ferreira et al., "Portable bioimpedance monitor evaluation for continuous impedance measurements. Towards wearable plethysmography applications," Conf Proc IEEE Eng Med Biol Soc 2013:559-562 (2013).
International Preliminary Reporton Patentability from International Application No. PCT/US2018/032984 dated Nov. 19, 2019.
International Search Report and Written Opinion from International Application No. PCT/US2018/032984 dated Aug. 3, 2018.
Jaeger et al., "Continuous assessment of cerebrovascular autoregulation after traumatic brain injury using brain tissue oxygen pressure reactivity," Crit Care Med 34(6):1783-1788 (2006).
Lam et al., "Monitoring of autoregulation using laser Doppler flowmetry in patients with head injury," J Neurosurg 86(3):438-445 (1997).
Lazaridis et al., "Optimal cerebral perfusion pressure: are we ready for it?," Neurol Res 35(2):138¬148 (2013).
Metzger et al., "Intrathoracic Pressure Regulation Improves Cerebral Perfusion and Cerebral Blood Flow in a Porcine Model of Brain Injury," Shock 44(1):96-102 (2015).
Nyboer, "Electrical Impedance Plethysmography; A Physical and Physiologic Approach to Peripheral Vascular Study," Circulation 2(6):811-821 (1950).
Shaw et al. "Investigation of the relationship between transcranial impedance and intracranial pressure," Acta Neurochir Suppl. 2012;114:61-5.
Shaw et al., "Investigation of the Relationship Between Transcranial Impedance and Intracranial Pressure," Acta Neurochir Suppl 114:61-65 (2012).
Steiner et al., "Continuous monitoring of cerebrovascular pressure reactivity allows determination of optimal cerebral perfusion pressure in patients with traumatic brain injury," Crit Care Med 30(4):733-738 (2002).
Tackla et al., "Assessment of Cerebrovascular Autoregulation Using Regional Cerebral Blood Flow in Surgically Managed Brain Trauma Patients," Neurocrit Care 23(3):339-346 (2015).
Underwood, "Cadaver study challenges brain stimulation methods," Science 352(6284):397 (2016).
Zweifel et al., "Continuous monitoring of cerebrovascular pressure reactivity in patients with head injury," Neurosurg Focus 25(10):E2, 8 pages (2008).

* cited by examiner (to be continued)

(to be continued)

(to be continued)

(continuation)

OCULAR IMPEDANCE-BASED SYSTEM FOR BRAIN HEALTH MONITORING

CROSS-REFERENCE TO RELATED APPLICATION

This application claims the benefit of U.S. Provisional Application No. 62/506,971, filed May 16, 2017, entitled "Ocular Impedance Based System for Brain Health Monitoring," which is hereby incorporated by reference in its entirety.

FIELD OF THE DISCLOSURE

The present disclosure relates generally to techniques for monitoring and assessing brain health and, more particularly, to techniques for using an ocular impedance measurement to monitor and assess brain health.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Traumatic brain injury (TBI) plays a major role in approximately 30% of injury related deaths in the United States and is often referred to as the "silent epidemic" due to associated complications that go undiagnosed and unnoticed, but that may have a lasting effect on health. Management strategies in the treatment of severe-TBI are usually aimed at preventing secondary brain injury, which mainly manifests itself as inflammation and brain ischemia. Monitoring of intracranial pressure (ICP) and optimization of cerebral perfusion pressure (CPP) to a target level have been proposed in the past as primary methods to prevent secondary injury and are the backbones of current practice. However, recent trials did not demonstrate clear benefits of ICP monitoring or targeted CPP to guide management.

Recent management approaches have attempted to utilize a more dynamic, and individualized precision optimization of CPP based on cerebrovascular autoregulation (CAR) using methods such as pressure reactivity index (PRx). Autoregulation is the ability of vessels to modulate their tone in response to changes in CPP and in so doing, maintain constant levels of cerebral blood flow (CBF) to match cerebral metabolic demand. CAR can be considered one of the most important central nervous system auto-protective mechanisms against secondary brain injury. It is often impaired after severe-TBI and has been shown to be a predictor of outcome in patients with severe-TBI as well as various acute neurological diseases and ischemic injuries such as stroke, subarachnoid hemorrhage, brain tumors, cardiac arrest, hypertensive crises, and others.

However, current assessment methods of CAR lack the ability to directly monitor and track relative changes in cerebral blood volume. In addition, they cannot be utilized in settings outside the hospital. For example, current techniques using PRx require invasive monitoring.

There is a need for a technique that can be used to monitor dynamic changes in cerebral blood volume (CBV) as a reflection of CAR. There is a need for a portable, non-invasive sensor for measuring CBV changes in casualties with traumatic head injury and other cerebrovascular emergencies, suitable for use in varied environments (e.g., in civilian and military prehospital settings, emergency department trauma centers, intensive care units, etc.). This will allow early precision monitoring and treatment to prevent secondary brain damage.

SUMMARY OF THE INVENTION

The present techniques include methods and systems that monitor and assess brain bioimpedance through an ocular window as a method of assessing dynamic changes in cerebral blood volume (CBV). The techniques may be achieved in a non-invasive and continuous manner. The techniques monitor brain impedance to track changes in CBF, ICP and CPP that are associated with changes in cerebral blood volume. In this way, the techniques may be additionally used to evaluate CAR impairment The present techniques provide a non-invasive way to measure numerous different brain health indicators using impedance measurements collected through the eye(s) of a subject. An ocular bioimpedance device is used to particularly localize measurement electrodes which may include combinations of cathodes and anodes.

In an example, an apparatus for evaluating brain health of a subject comprises: one or more electrodes; one or more processors; a computer-readable memory storing non-transient instructions that when executed by the one or more processors cause the apparatus to: provide, using the one or more electrodes, electrical current to an ocular region of the subject; sense, using the one or more electrodes, an electrical signal obtained from the ocular region of the subject, and determine a bioimpedance value of the subject from the electrical signal, wherein the bioimpedance value represents a bioimpedance for a conduction path that includes at least a portion of the ocular and brain regions of the subject; and determine a brain health indicator from the bioimpedance information.

In another example, a method of evaluating brain health of a subject, the method comprising: in response to the provision of an electrical signal to an ocular region of a subject and detection of the electrical signal over a conduction path that includes at the ocular region and at least a portion of a brain region, determining an ocular-brain region bioimpedance value of the subject; determining, from the ocular-brain region bioimpedance value, changes in intracranial pressure over a sample time period, those changes corresponding to changes in cerebral blood volume (CBV); determining the effects of arterial pressure of the subject on CBV over the sample time period; determining the effects of mean intracranial pressure over the sample time period and mean arterial pressure over the sample time period on CBV; and determining a pressure reactivity index value from a correlation of the mean intracranial pressure and the mean arterial pressure, the pressure reactivity index on CBV indicating the brain health of the subject.

In another example, a method of evaluating brain health of a subject, the method comprising: receiving mean intracranial pressure data of the subject over a sample time period; receiving mean arterial pressure data for the subject over the sample time period; receiving a pressure reactivity index value determined from a correlation of the mean intracranial pressure and the mean arterial pressure, the pressure reactivity index indicating a brain health of the subject; in response to the provision of an electrical signal to an ocular region of the subject and detection of the electrical signal over a conduction path that includes at the ocular region and at least a portion of a brain region, determining an ocular-brain region bioimpedance of the subject over the sample time period; and combining the bioimpedance with the pressure reactivity index and producing a brain health indicator, the indicator having a positive value indicating a healthy brain state of the subject and a negative value indicating an unhealthy brain state of the subject.

In another example, a method of treating a brain condition of a subject, the method comprising: applying, to an ocular region of the subject, a brain-condition affecting treatment to the subject, the brain-condition affecting treatment being a transcranial direct current stimulation (tDCS), a transcranial alternating current stimulation (tACS), a biophotonic stimulation, and/or an acoustic stimulation.

In another example, an apparatus for treating a brain condition of a subject, the apparatus comprising: a housing configured to engage an ocular region of the subject, the housing having one or more electrodes configured to deliver electrical signals to the ocular region of the subject; one or more processors; a computer-readable memory storing non-transient instructions that when executed by the one or more processors cause the apparatus to: supply, using the one or more electrodes, an electrical signal in the form of a transcranial direct current stimulation (tDCS) and/or a transcranial alternating current stimulation (tACS) to the ocular region of the subject to treat the brain condition.

BRIEF DESCRIPTION OF THE DRAWINGS

The figures described below depict various aspects of the system and methods disclosed herein. It should be understood that each figure depicts an example of aspects of the present systems and methods.

FIG. 5A) illustrates an example, measured impedance response during normal breathing. FIG. 5B) illustrates an example, measured impedance response during deep Breathing. FIG. 5C) illustrates an example, measured impedance response during a Valsalva maneuver. FIG. D) illustrates an example, measured impedance response while holding ones breath. Images scales vary change to allow visual inspection of the changes.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Figure 5:
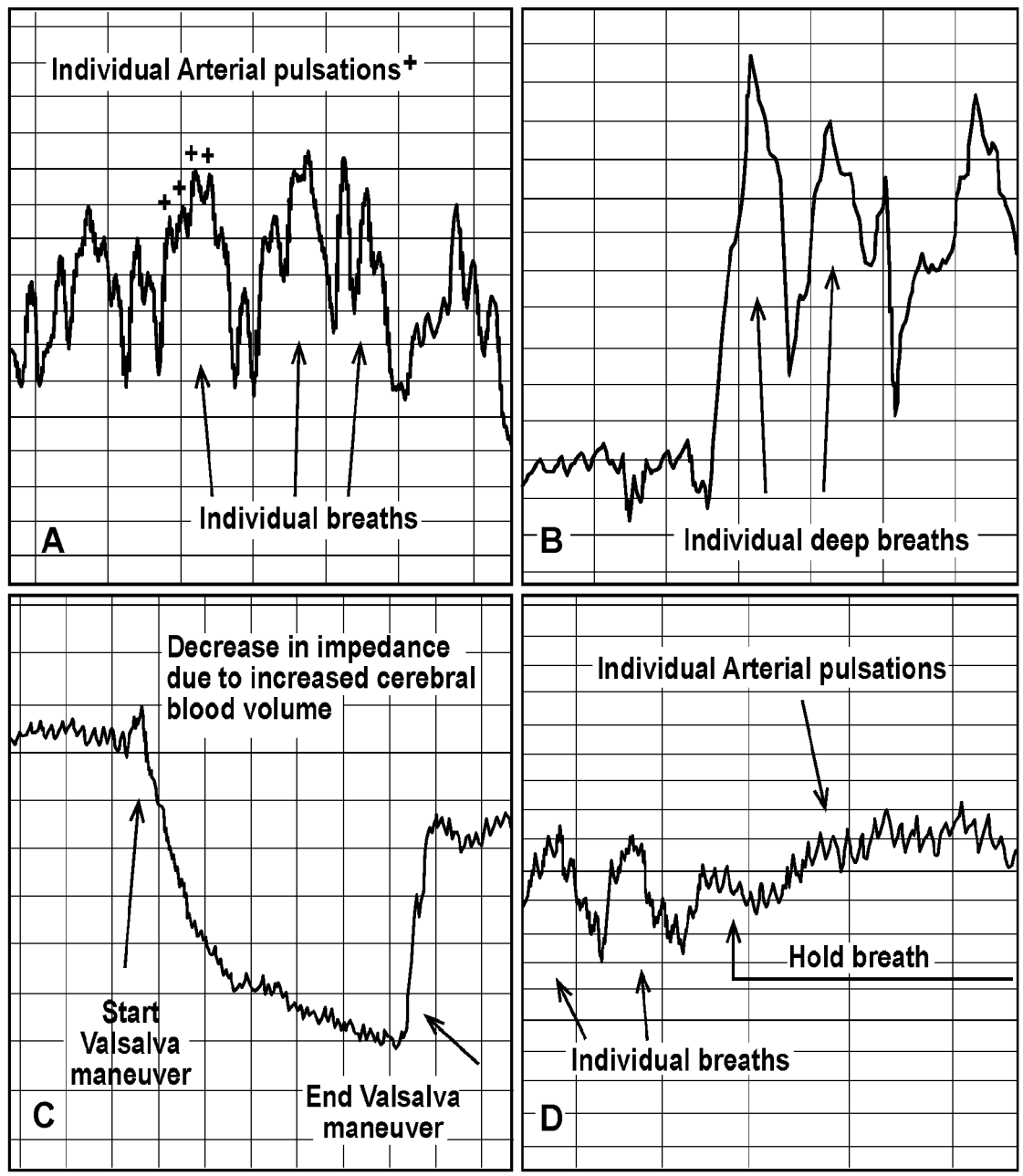
FIG. 5 illustrates plots of brain-ocular impedance measurements obtained from ocular impedance electrodes.
Figure 6:
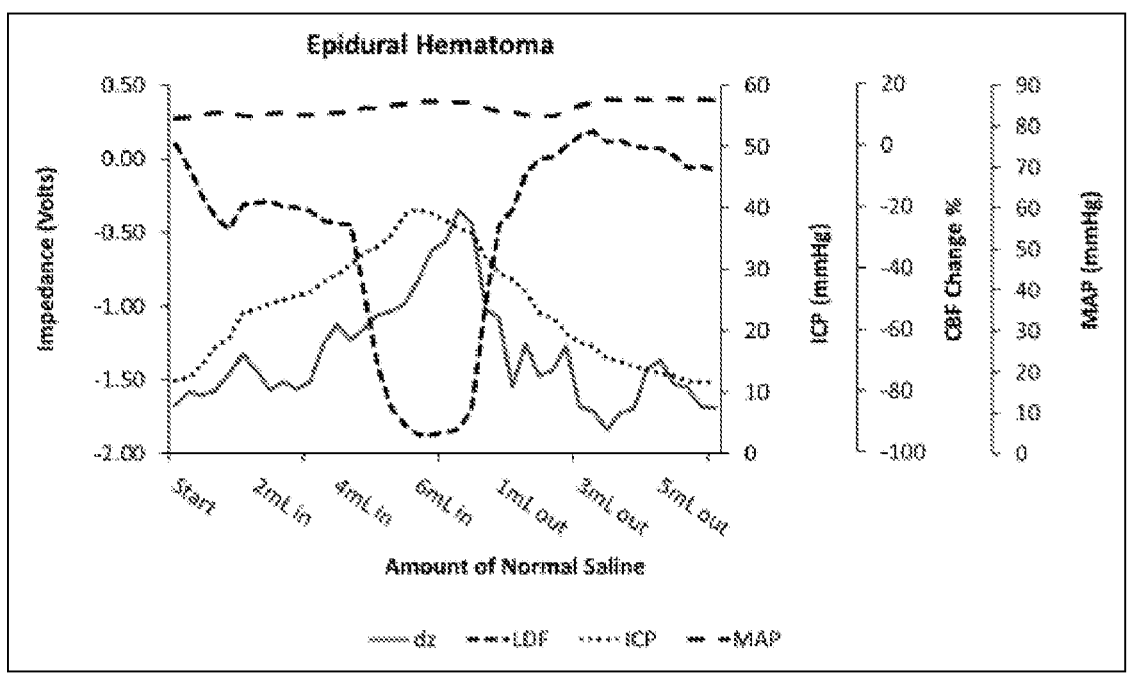
FIG. 6 illustrates changes in ICP, CBF, MAP and impedance during induction of epidural hematoma (in) then during removal of hematoma (out).

Bioimpedance is a measure of tissue resistance to an induced current or voltage. When the current is applied to the body, either as a whole or a portion thereof, bioimpedance will represent a cumulative effect of the impedances of each of the components through which the current flows. These components might include muscle tissue, bone, fat, intracellular and extracellular fluid, and blood. Blood, being a good conductor, has a distinct effect on impedance. Hence, physiologic or other induced events which modulate blood volume in an area of interest can be detected with impedance. An example of this is the effect of ventilation and even the cardiac cycle (FIG. 5). Therefore, the electrical impedance across a segment of tissue increases with decreased blood volume and decreases with increased blood volume. For example, the Valsalva maneuver is expected to increase cerebral volume (and hence reduce impedance) by increasing venous pressure and limiting venous return from the brain. Deep breathing is expected to demonstrate large swings in impedance as deep inhalation increases venous return from the brain, whereas breath holding is expected to minimize respiratory induced changes. The plots of FIGS. 5A-5D provide examples. FIG. 6 illustrates trends and changes over time for MAP, ICP, CBF and impedance during the creation then removal of an epidural hematoma, a type of traumatic brain injury. As the plots of FIG. 6 demonstrate, impedance (dz) increases with decreased blood volume (i.e., decreased CBF) and vice versa.

The present techniques provide methods and systems to measure brain bioimpedance through the eyes, or other portions of the ocular region, using a bipolar arrangement. Example ocular bioimpedance devices are illustrated in FIGS. 7-9, 11, and 12. Because of the fluid interface and close proximity of the ocular bioimpedance devices to the brain along with a decrease in intervening tissues (hair, scalp, muscle, bone) and the direct connection of the ocular nerve to the brain, the present devices are able to ensure that the brain will encounter a significant portion of the electrical current sent through the devices. As small current may be applied through the eyes and the resulting the measured conductivity differences reflect the blood volume between the electrodes, which will include a large portion of the brain.

As discussed further herein, we've confirmed the assessment of bioimpedance through ocular measurements using various experimental maneuvers, such as through increasing ICP using inflation of the epidural balloon to demonstrate that changes in scalp or facial soft tissue blood flow are not responsible for the noted changes in impedance measured by the present techniques. In this way, we demonstrate an entirely new bioimpedance pathway measurement, uncorrelated to conventional scalp-based measurement techniques and heretofore unrecognized and un-isolated for measurement and assessment. Further, the present techniques provide unexpected improvement in measuring bioimpedance and correlating that measurement to indicators of brain health, such as CBF, ICP and CPP.

Various experimental maneuvers (hyperventilation, vasopressors infusion, epidural hematoma and systemic hemorrhage) were used to vary the level of cerebral blood volume through changes in ICP, CPP and CBF for testing the efficacy of the present techniques. In each case, the ocular impedance measurement technique was able to detect changes in cerebral blood volume associated with the events. These tests demonstrated the ability of the present techniques to provide an effective mechanism for evaluating CAR and other intracranial events by monitoring changes in cerebral blood volume through impedance. As such, the techniques herein can be used to provide early evaluation of a patient with TBI or other cerebral insult, as a mechanism to evaluate CAR or the effect of other therapies on changes in cerebral blood volume prior to performing an invasive monitoring procedure on the patient or in conjunction with such invasive monitoring.

Furthermore, the present techniques may be combined with other monitoring techniques. For example, approaches such as calculation of the pressure reactivity index (PRx) (a moving Pearson correlation between mean arterial pressure MAP and ICP) have been shown to provide an independent predictor of brain health. The ocular measurement, bioimpedance techniques herein may be used in conjunction with PRx, where using an additional simultaneous measure such as cerebral impedance may allow improved use of PRx, which is an otherwise high noise measurement. Although overall tissue impedance changes over time, varies among individuals, and might be affected by the type and placement of electrodes (cathodes and anodes), the present techniques may reduce these effects by normalizing the impedance wave to its basal value negating the need to index to a baseline or normal value. Furthermore a PRx type measure utilizing MAP and cerebral impedance (using a moving Pearson correlation or other computational techniques) may be used as a precision measure of CAR.

The techniques herein can be used with PRx, and CAR more broadly in a number of ways. In some examples, the bioimpedance measurement techniques herein are used to determine ICP from which a more accurate PRx value can be determined, and a more accurate assessment of CAR results. In other examples, PRx may be determined independently, for example through known techniques, and the PRx value may be correlated with bioimpedance for a more accurate assessment of CAR.

As an example embodiment, PRx is determined independently and then correlated with bioimpedance measured using the techniques described herein. For example, the bioimpedance can be combined with the pressure reactivity index to produce a brain health indicator, where, like the PRx value itself, that indicator having a negative value indicates a healthy brain state of the subject (i.e., an intact autoregulation) and the indicator having a positive value indicates an unhealthy brain state of the subject (i.e., an impaired autoregulation). The combination is a mathematical combination. For example, where the two values can be correlated over a sample time period using a moving Pearson correlation. Additionally, a moving Pearson correlation could be produced using MAP and dz measured by bioimpedance allowing both PRx and the additional MAP and dz correlation to be compared and tracked together.

We describe example testing procedures below. In a first example, we measured brain bioimpedance using an ocular-brain interface in a novel manner to assess real time changes in cerebral blood volume in response to a number of physiologic challenges. As blood is a good conductor of electricity, we hypothesized that changes in brain bioimpedance (dz) would track changes in cerebral blood volume. Six anesthetized swine were instrumented for invasive monitoring of ICP, mean arterial blood pressure (MAP), cerebral perfusion pressure (CPP) and cerebral blood flow (CBF). Bioimpedance was monitored continuously through ECG electrodes placed over the eyelids. Low current (0.1-1 mA, at 50 kHz) was applied and the electrical potential sensed through the same electrodes. Interventions such as hyperventilation, vasopressor administration, creation of an epidural hematoma, and systemic hemorrhage were used to manipulate levels of ICP, CPP, and CBF.

The results of the testing showed that bioimpedance (dz) is highly correlated to changes in ICP, CPP, and CBF ($r=-0.72$ to $-0.88$, $p<0.0001$). The Receiver Operator Curve (ROC) for dz was plotted at different thresholds of CPP and percent change in CBF. The Area Under the Curve (AUC), sensitivity and specificity were calculated for each threshold. dz was shown to have a high predictive power with areas under the curve between (0.80-1.00, $p<0.003$) with sensitivity and specificity varying between (83%-100%) and (70%-100%) respectively demonstrating the ability of dz to track changes in cerebral blood volume in real time.

Thus these experiments confirmed brain bioimpedance measured through the ocular brain interface can be used to track changes in CPP and CBF with high precision and are valuable assessing changes in cerebral blood volume and CAR.

Hyperventilation: The mechanical ventilator was initially set at baseline between 15-18 BPM to achieve an end tidal CO2 (PetCO2) at 35-40 mmHg. After baseline line readings, the respiratory rate (RR) was then increased fourfold in increments of 10 breaths until PetCO2 reached ~20 mmHg. PetCO2 was maintained at ~20 mmHg for 5-10 min. RR was then decreased to baseline levels.

Vasopressor (norepinephrine) administration: Norepinephrine (4 μg/ml) was mixed with 500 mL of 5% dextrose, administered by continuous infusion and titrated to reach an MAP of 160 mmHg or greater. MAP was maintained at 160 mmHg or greater for 5 minutes followed by stopping the infusion and allowing the animal's MAP to return to near baseline level. The norepinephrine infusion was repeated three times.

Epidural Hematoma: Simulation of an epidural hematoma was created using an 8F Foley catheter as described by Metzger and colleagues. The balloon was filled with 6-8 mL of normal saline at a rate of 0.5 mL/min. ICP was monitored as the balloon was inflated to reach an ICP of 35-45 mm Hg. The pressure was maintained for up to 5 min followed by deflating the balloon at the same rate to bring ICP back to baseline level.

Systemic Hemorrhage: Lastly, animals were hemorrhaged through the femoral artery at a rate of 50-100 mL/min. Hemorrhage continued uninterrupted for 16-20 minutes for a total volume of 800-1000 mL representing 30-40% of the animals' estimated total blood volume.

In another experiment, three human subjects were consented and had electrodes placed on their closed eyelids for impedance monitoring using the same current and impedance monitoring parameters described in the animal experiments. Volunteers were placed in a supine position and then asked to perform the following maneuvers: normal breathing, deep breathing, breath holding, and Valsalva maneuvers.

We examined and evaluated changes in ocular-brain impedance as well as cerebral and systemic hemodynamics (CBF, ICP, CPP, MAP, PetCO2) throughout baseline and during the various maneuvers. The raw impedance signal was initially smoothed and filtered using an iterative simple moving average (three passes through a 20 point moving average). Impedance changes (dz) were calculated as $dz = (z_{max} - z_{min})/z_{max}$ then transformed using the natural logarithm.

For the two experiments, descriptive statistics used to assess effectiveness and to present means and standard deviations (SD), or median and interquartile ranges (IQR). A number of statistical analyses were utilized to compare the performance of dz with the invasive measures of MAP, ICP, CBF, CPP and PetCO2 as follows. Pearson correlation was used to allow for visual inspection across a range of values. Receiver-Operator Characteristic (ROC) analysis and Area Under the Curve (AUC) were constructed to assess the predictive value of dz across a certain range of CBF and CPP values. The ROC graph depicts the relationship between true positive and false positive results; the greater the AUC, the better the predictive value. Significance level was considered at $\alpha=0.05$.

Figure 1:
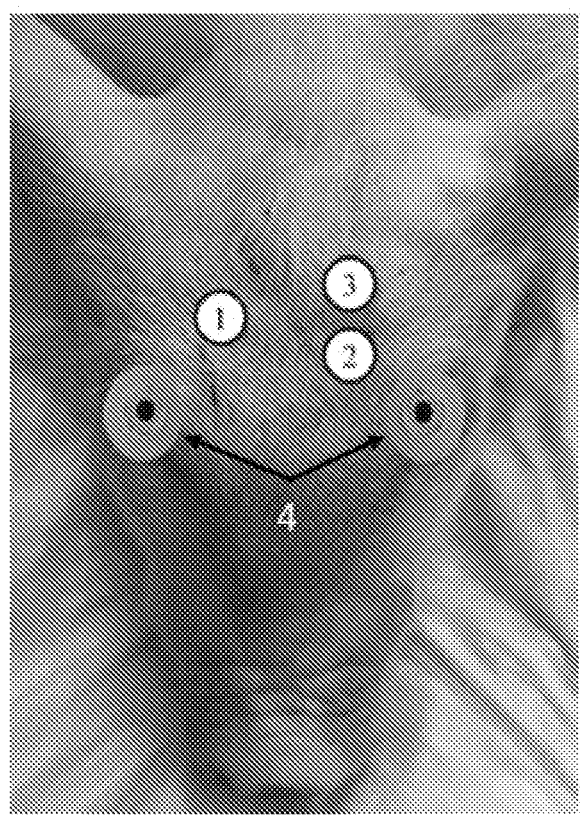
FIG. 1 illustrates the placement on a test subject of a Foley catheter balloon (1), an ICP probe (2), a LDF probe (3) and ocular impedance electrodes (which may include combinations of cathodes and anodes) (4).
Figure 2:
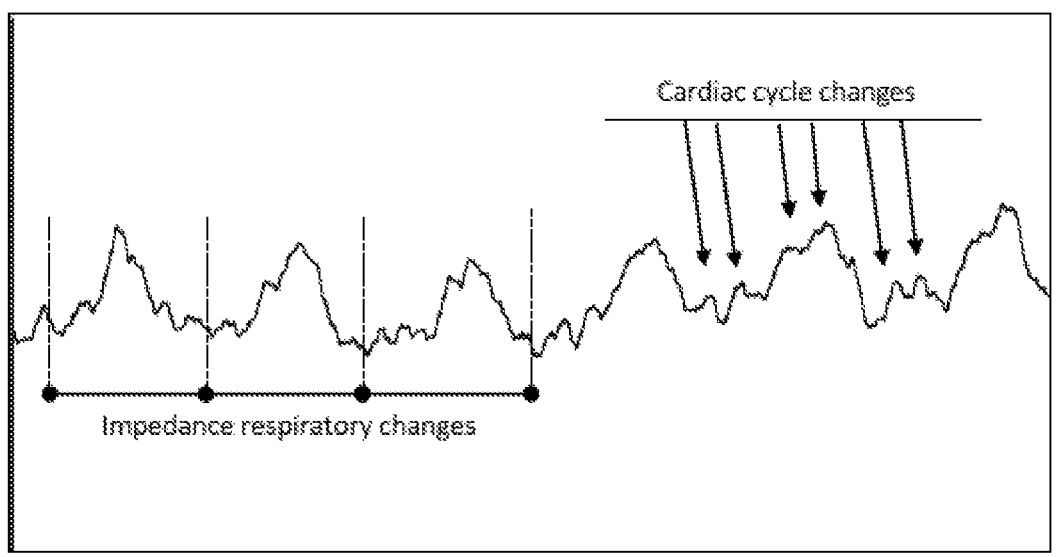
FIG. 2 is a plot of impedance waveform showing respiratory as well as cardiac cycle changes as measured using ocular impedance electrodes, in an example.
Figure 3:
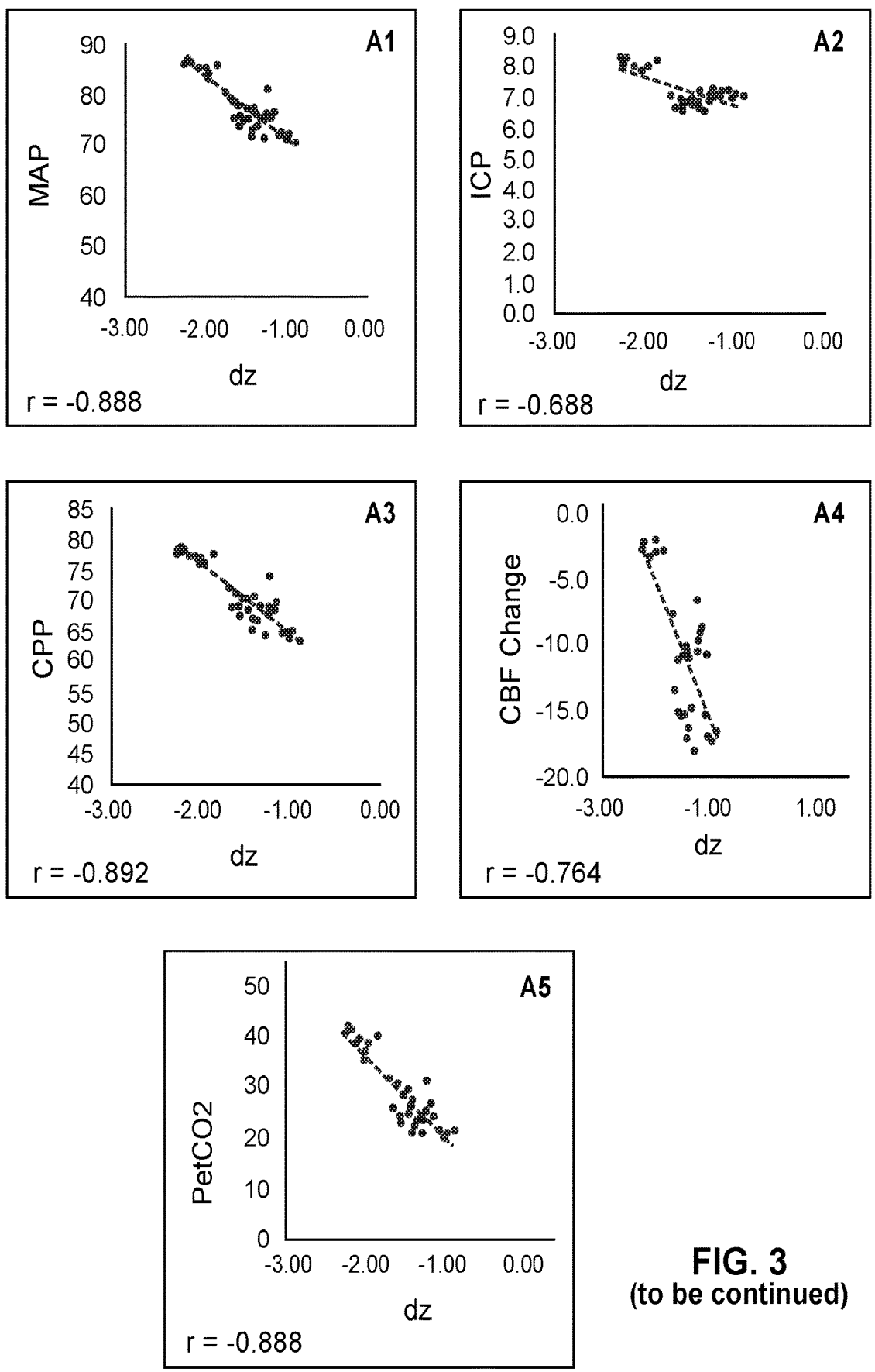
FIG. 3 illustrates scatter plots and correlation coefficients for A: During hyperventilation, Plot A1) dz vs. MAP, Plot A2) dz vs. ICP, Plot A3) dz vs. CPP, Plot A4) dz vs. CBF Change and Plot A5) dz vs. PetCO2. B: During vasopressors infusion, Plot B1) dz vs. MAP, Plot B2) dz vs. ICP, Plot B3) dz vs. CPP and Plot B4) dz vs. CBF Change. C: During epidural hematoma, Plot C1) dz vs. ICP, Plot C2) dz vs. CPP, Plot C3) dz vs. CBF change. and D: During systemic hemorrhage, Plot D1) dz vs. MAP, Plot D2) dz vs. ICP, Plot D3) dz vs. CPP and Plot D4) dz vs. CBF Change, where dz is the measured brain bioimpedance, MAP is the mean arterial pressure, ICP is the intracranial pressure, CPP is the cerebral perfusion pressure, and CBF is the cerebral blood flow.
Figure 3:
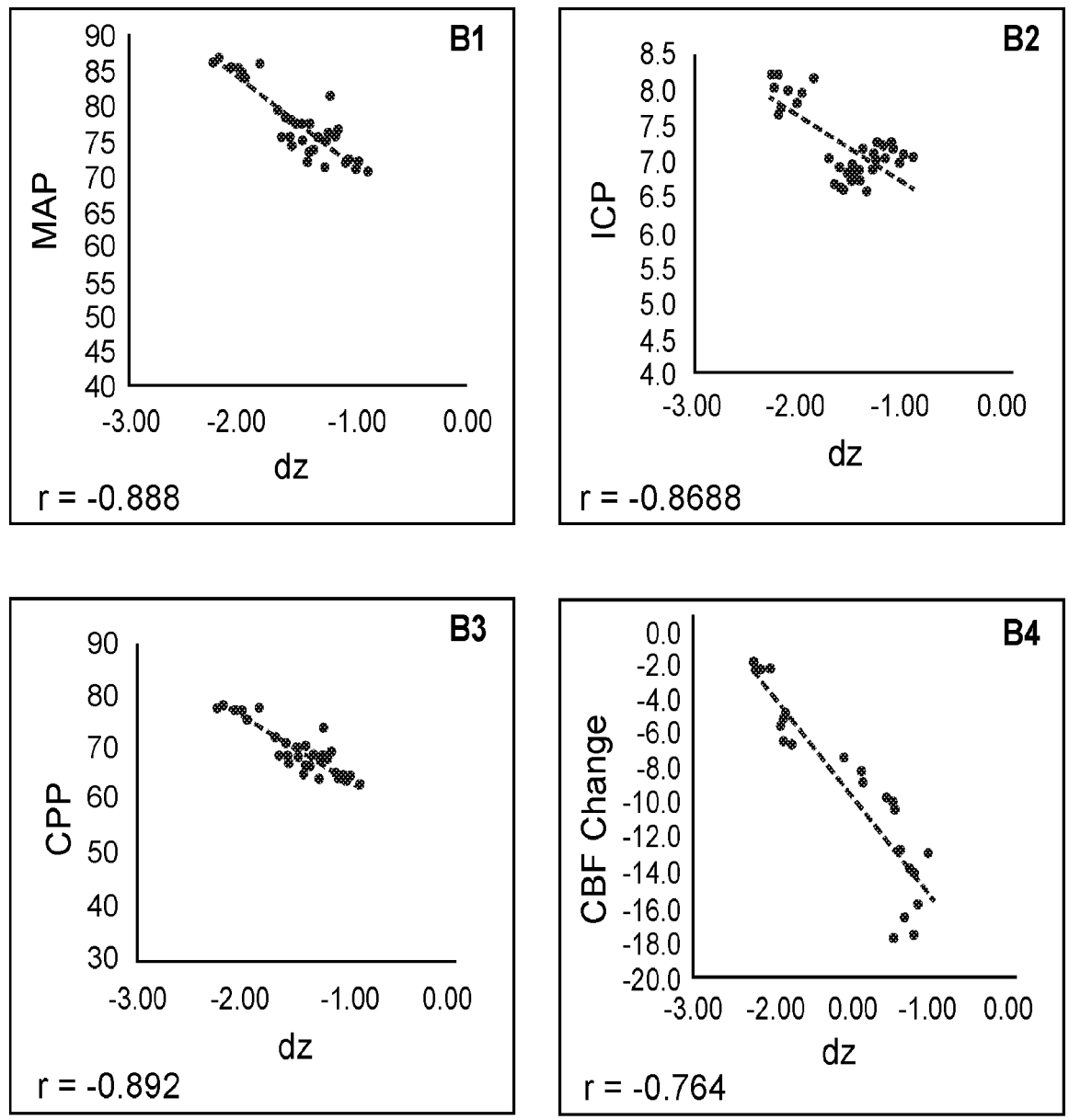
Figure 3:
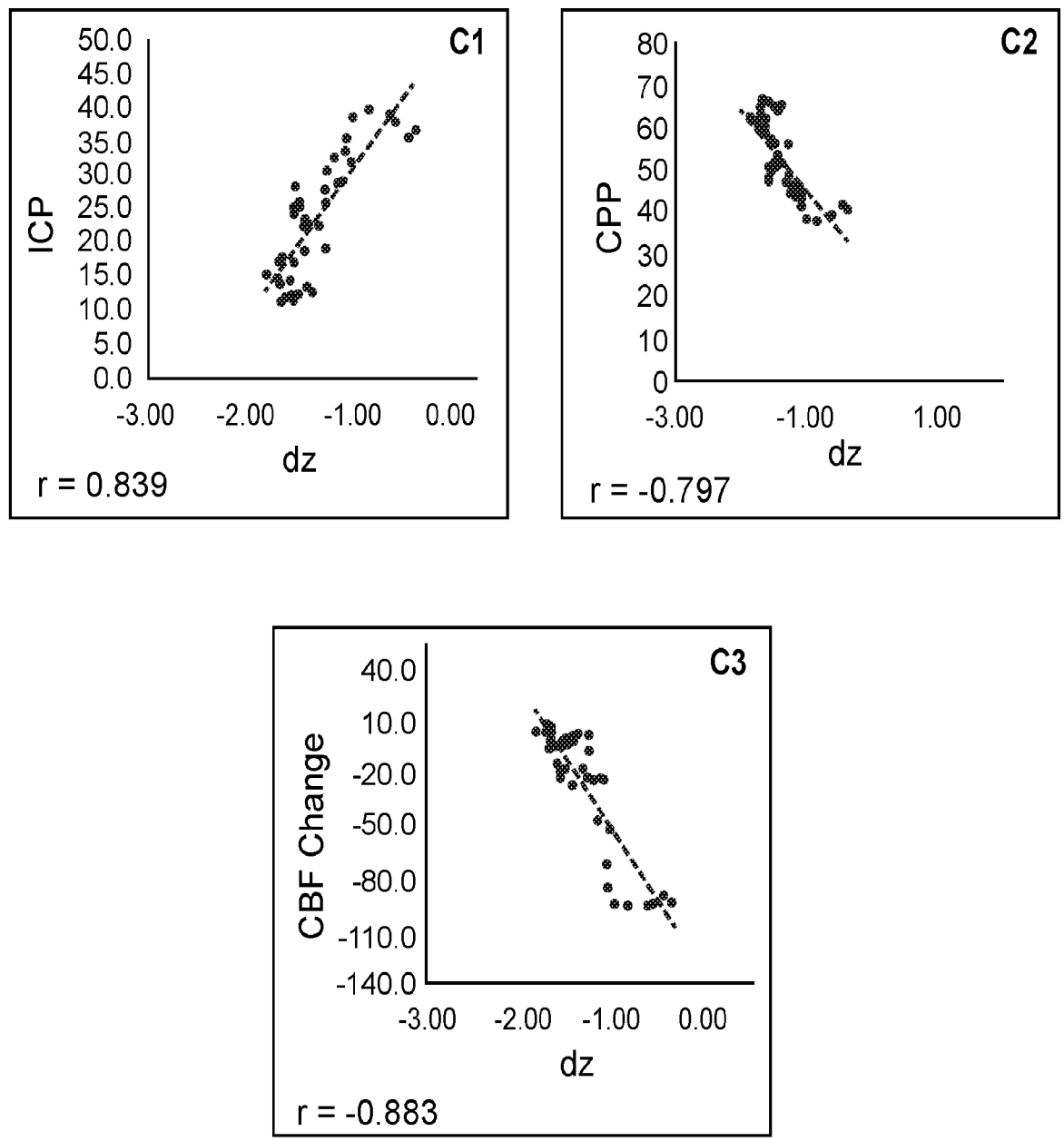
Figure 3:
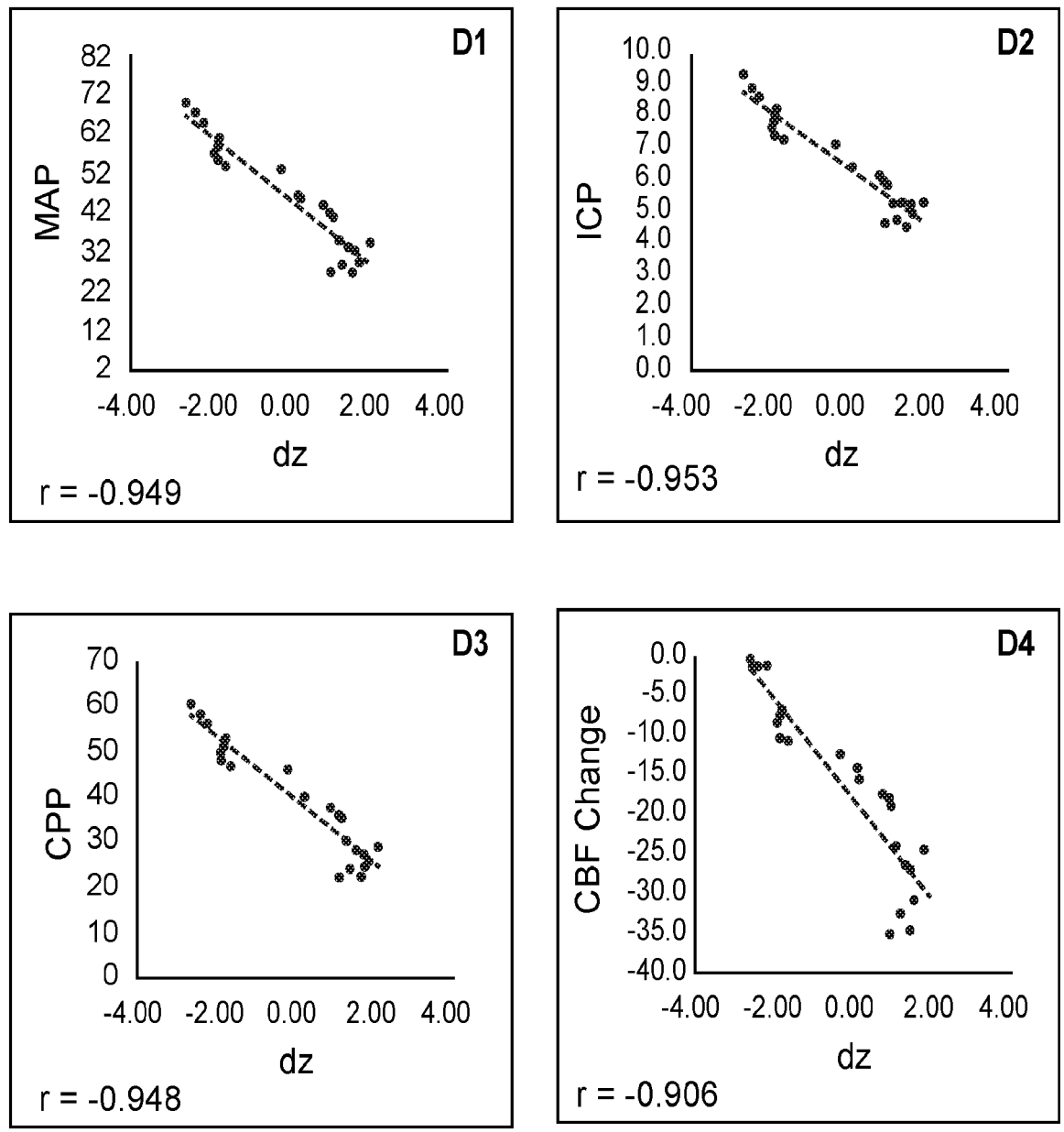

The results were as follows. For the first experiment, six animals with an average (SD) weight of 39.3(0.75) kg were tested. FIG. 2 demonstrates a baseline ocular-brain bioimpedance recording during mechanical ventilation noting both changes induced by respiration as well as superimposed cardiac cycle changes. Table 1 shows mean and (SD) values for weight MAP, ICP and CPP at baseline as well as range (minimum and maximum) and direction of changes during the various maneuvers. Pearson correlation showed high correlation between MAP, ICP, CPP, PetCO2, CBF change and dz (r=0.6 to 0.96, p<0.0001) (see, Table 1 and FIG. 3).

The ROC for dz during maneuvers was plotted at different thresholds of CPP and CBF changes. As shown in Table 2, AUCs, sensitivity and specificity were calculated for dz at each maneuver. dz demonstrated a high prediction capability with areas under the curve between (0.81-1.00, p<0.004). The sensitivity and specificity of the impedance method associated with the above thresholds varied between (0.75-1.00) and (0.80-1.00) respectively. Table 2 lists various CPP and percent CBF change thresholds, and corresponding AUCs sensitivities and specificities for dz during maneuvers.

Figure 4:
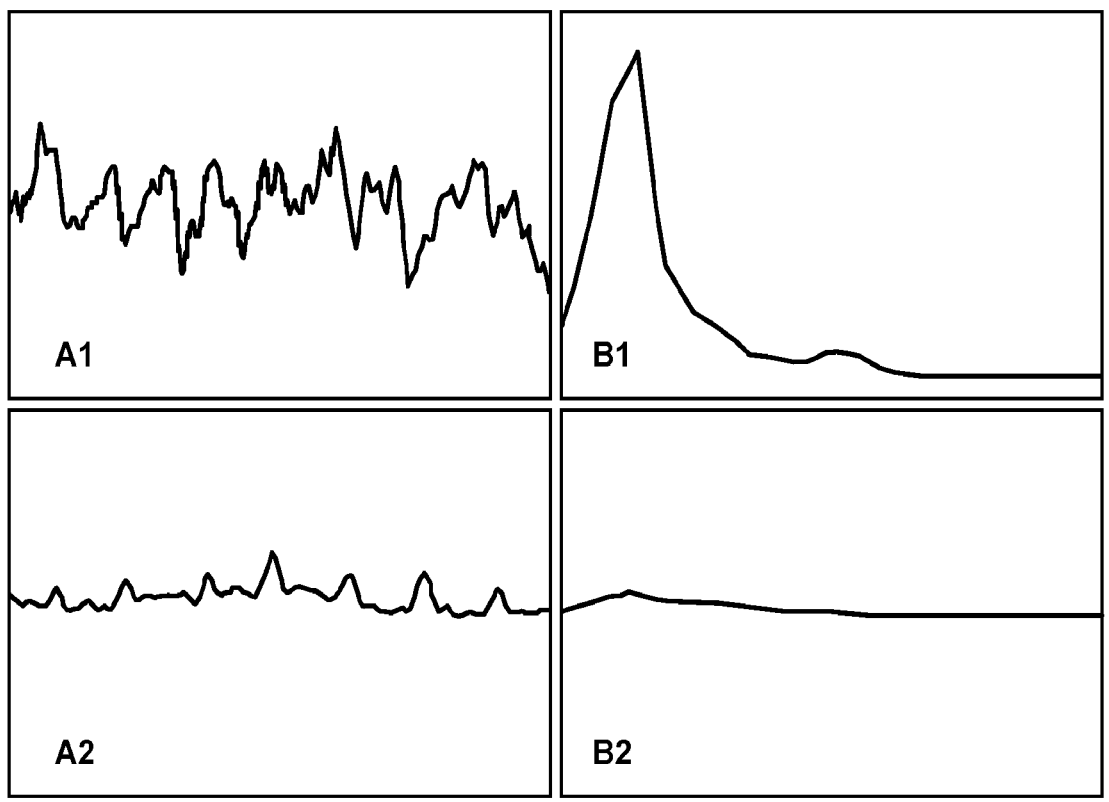
FIG. 4 illustrates plots of an impedance waveform obtained with ocular impedance electrodes (cathode and anode) placed on various locations, namely plot A1) eyelids and plot A2) on scalp as well as the power spectral density for plot B1) ocular impedance and plot B2) scalp impedance, respectively. The plots use the same scale.

In order to better understand and quantitate the ability of the ocular pathway technique to incorporate or capture signal from the brain compared to scalp, we performed a separate experiment in one additional animal. The effectiveness of ocular current injection was compared to injection of the same amount of current through the scalp by placing one pair of electrodes on the eyelids and another pair close to the animal's ears with the same distance as the first pair. First, the resistance between the ocular and scalp electrodes was measured. Injecting current through the ocular path resulted in a resistance of 0.5 MΩ compared to 3 MΩ, when current is injected into through the scalp indicating significantly better conductance through ocular injection of current. Next, the power spectral density was used to compare the amplitude of the respiratory component of dz (see, FIG. 4). The tidal respiration was controlled by the ventilator at rate of 16 breaths per minute. The power of the respiratory component was 6.5 times larger when the current was injected through the ocular path compared to the scalp path. The ratio was increased to 46 times when the animal was hyperventilated (RR=56).

The voltage gradient was then measured inside the brain by creating two burr holes in the skull, equally distanced between the ocular and scalp electrodes. The voltage gradients exerted by the current were measured by periodically interrupting the current injection. This was repeated 20 times and averaged using each pair of the electrodes. The results showed that the voltage gradient inside the brain was 40% higher when the current was injected through the ocular path compared to the scalp pathway, indicating that a larger portion of the current passes through the brain if current is injected through the ocular pathway. Finally, the animal was euthanized and the resistance between the two eyelids was measured absent of the electrical variations caused by brain activity and changes in the blood flow. This was repeated after a craniotomy was performed and the brain was removed followed by return of the removed cranium and scalp which was sutured back in place. The resistance values were $R_T=10$ kΩ before and $R_S=30$ kΩ after the brain was removed. Assuming a parallel model for the resistance of the brain and the remaining tissue, skin and bone between the eyelids, the resistance of the brain was computed as $R_B = R_T R_S/(R_S - R_T) = 300/20$ kΩ $= 15$ kΩ. As a result, the ratio of current that passes through the brain to total current can be computed as $I_B/I_T = R_T/R_B = 10/15$. Hence, approximately two thirds of the current that is injected through the ocular pathway passes through the brain. While the current values for the electrical signal will vary for different subjects, with the improved techniques herein, bioimpedance can be measured from current values below about 10 mA, including below 5 mA, such as 4 mA and below or 2 mA and below. The lower bound of the current values will vary but may be 1 mA in some examples and even lower in other examples.

For the second experiment, the impedance data collected from the volunteer subjects demonstrated similar impedance waveforms noted from the animal experiments. Clear respiratory and cardiac cycle induced changes in the impedance waveform were observed. Deep inspiration and the Valsalva maneuver produced changes in impedance that would be expected from changes in cerebral blood volume produced by these respiratory maneuvers (see, FIG. 5).

Figure 7:
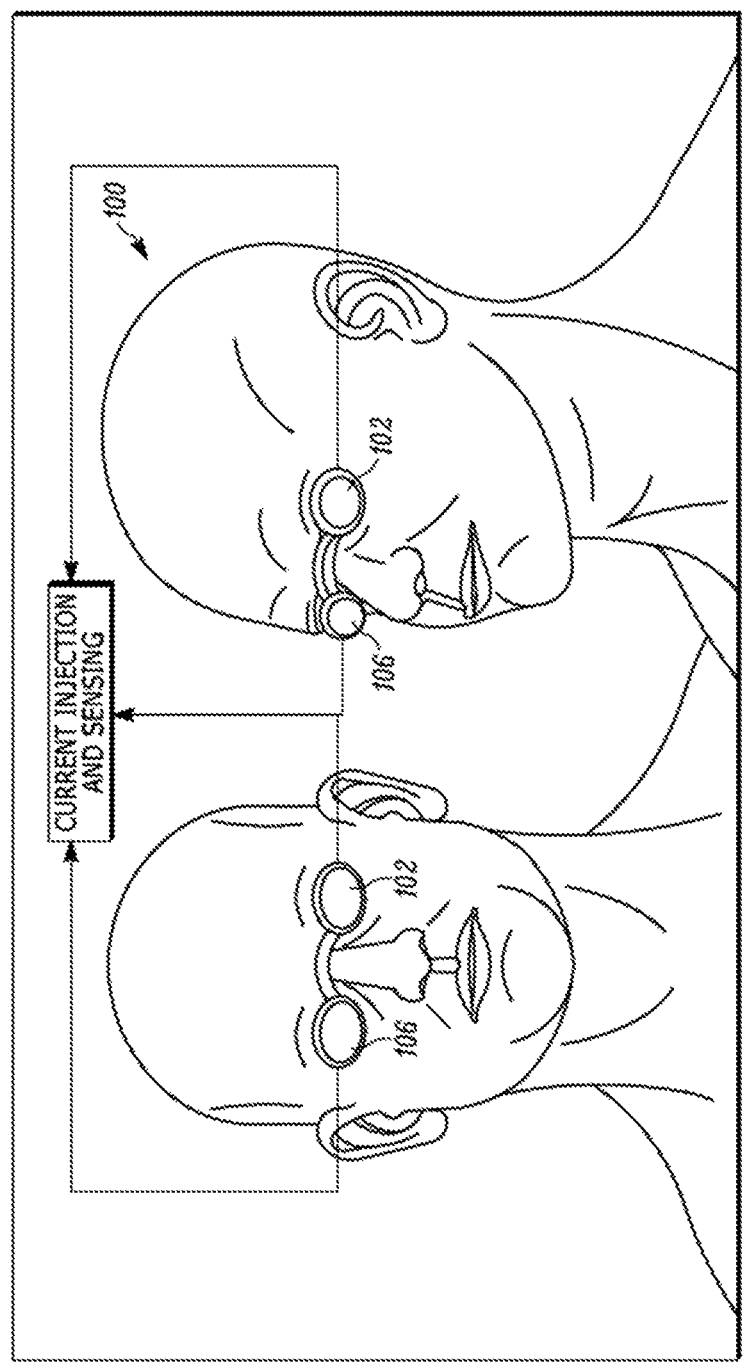
FIG. 7 illustrates an ocular bioimpedance measurement device, in accordance with an example.
Figure 8:
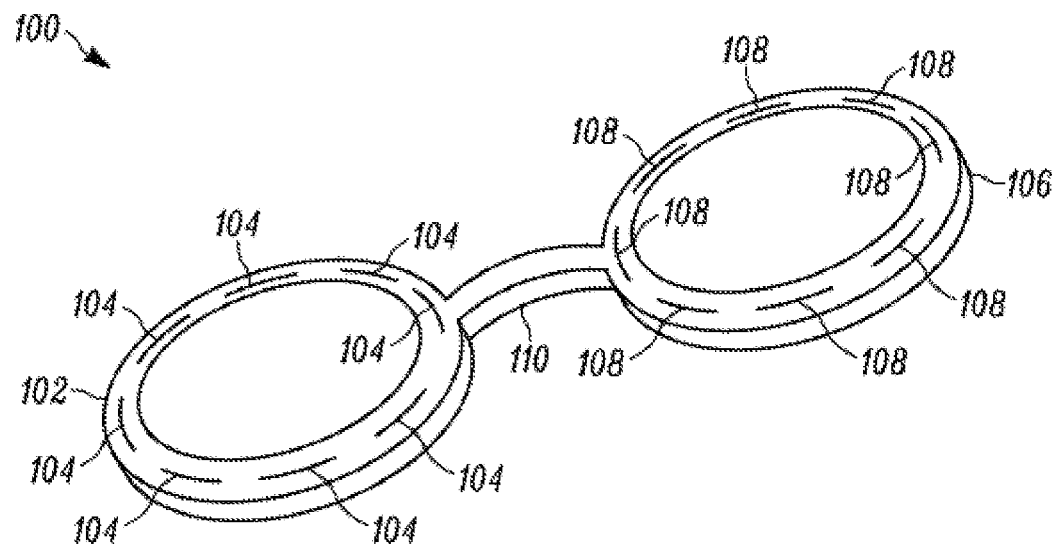
FIG. 8 illustrates an ocular bioimpedance measurement device, in accordance with another example.
Figure 9:
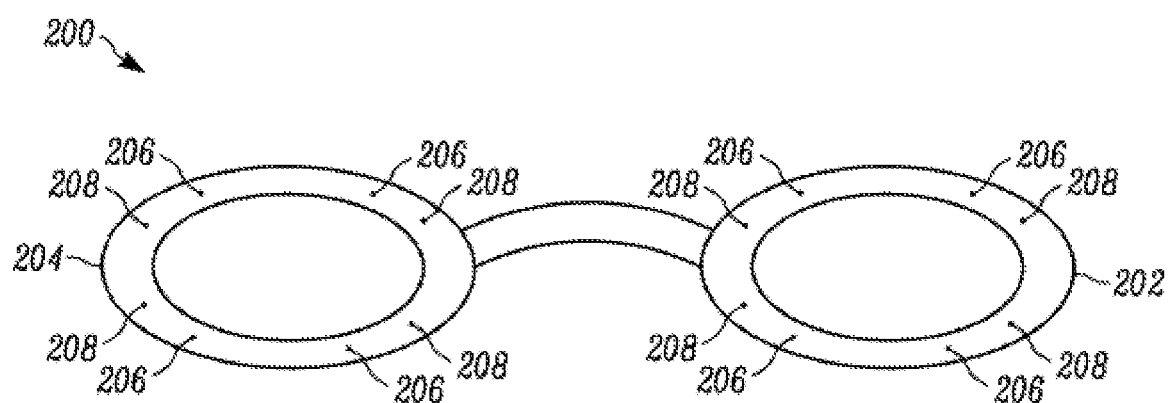
FIG. 9 illustrates an ocular bioimpedance measurement device, in accordance with another example.

FIGS. 7-9 (as well as FIGS. 11 and 12) illustrate different example ocular bioimpedance devices and configurations.

FIG. 7 illustrates an example ocular bioimpedance device 100 in the form of goggles having a first lens 102 formed of a cap that may transparent, partially transparent or opaque. In the illustrated example, the first lens 102 further includes one or more electrodes 104, shown in FIG. 8, on an interior ocular region engagement portion of the lens 102. The engagement portion is configured such that when the lens 102 is put in place on a subject, the one or more electrodes 104 are in conductive contact with surface skin of the subject. The one or more electrodes 104 provides a conduction path to the skin for injecting current to the subject at a point of contact within and thus through the skin of the ocular region of the subject. That conductive contact may be a direct contact with the skin (such as the close eyelids), such that the point of contact with the electrodes 104 is direct, or that point of contact may be through another electrical conductor positioned between the electrodes 104 and the skin, for example, through a conductive film positioned on or around the ocular region for dispersing the electrical current more uniformly to the patient. The device 100 includes a second lens 106 that may be similar or identical to the first lens 102 except that the electrodes in the second lens 106 may be configured for sensing the injected current from the first lens and thereby being used as a bioimpedance sensor. Electrodes 108 of the second lens 106 may be in direct contact with the skin or in indirect contact, like that of the electrodes 104. Furthermore, while the electrical current path is described as starting with lens 102 and terminating with lens 106, such orientation may be imposed by the control circuitry coupled thereto (see, e.g., FIG. 10). The control circuitry could reverse the current flow direction and the operation would be the same. In some examples, the electrodes 104 and 108 are not identical, but may differ in electrode pattern and/or positioning. In such examples, the particular direction of current injection and sensing may be established, at least in part, based on the differences in those electrodes. The lens 102 and 106 are physically connected by a bridge 110 formed for a non-conducting material to further provide proper electrical isolation of the electrodes 104 and 108.

FIG. 9 illustrates another example configuration of an ocular bioimpedance device 200 similarly formed of a first lens 202 and a second lens 204. For the device 200 each lens includes both injection electrodes 206 and sensing electrodes 208. The patterning of the electrodes 206 and 208 can vary in pattern and position, as well. In the illustrated example, the injection electrodes 206 are disposed closer to a centroid of each lens 202 and 204, while the sensing electrodes 208 are positioned distally further from the centroid. The converse orientation may be used instead. In some examples, the electrodes 206 and 208 may be positioned in an alternating manner around the engagement surface of the lens. As is the case for the device 100, in some examples, only one of each electrode type is used on each lens.

While examples are shown of a device in contact with the skin, in yet other examples, contact is achieved between the corneal tissue and the device in a contact lens type manner.

The ocular bioimpedance techniques herein may be implemented in devices offering a combination of features. For example, lens-based devices for measuring bioimpedance may be combined with lens based devices and also include light transmitters in the lens cap, transmitters that are able to provide light therapy to a patient, such as goggles that provide white light therapy through light emitting diodes (LEDs), high color temperature light therapy (500 lux, 1000 lux, 1500 lux, or higher), blue light therapy devices (e.g., emitting at wavelengths at or between 450 nm and 500 nm), various near infrared and infrared wavelengths (730-770 nm, 850-890 nm, 880-920 nm, 950-970 nm) for cerebral blood oxygenation monitoring, mitochondrial repair, and others. Some such devices are used to treat Seasonal Affective Disorder (SAD), as well as migraines and other brain related conditions. In yet other examples, the ocular bioimpedance techniques herein may be used with an acoustic energy application device, such as that described in U.S. Pat. No. 8,172,769, entitled "Method and apparatus for monitoring intra ocular and intra cranial pressure," the entire specification of which is hereby incorporated by reference.

Figure 10:
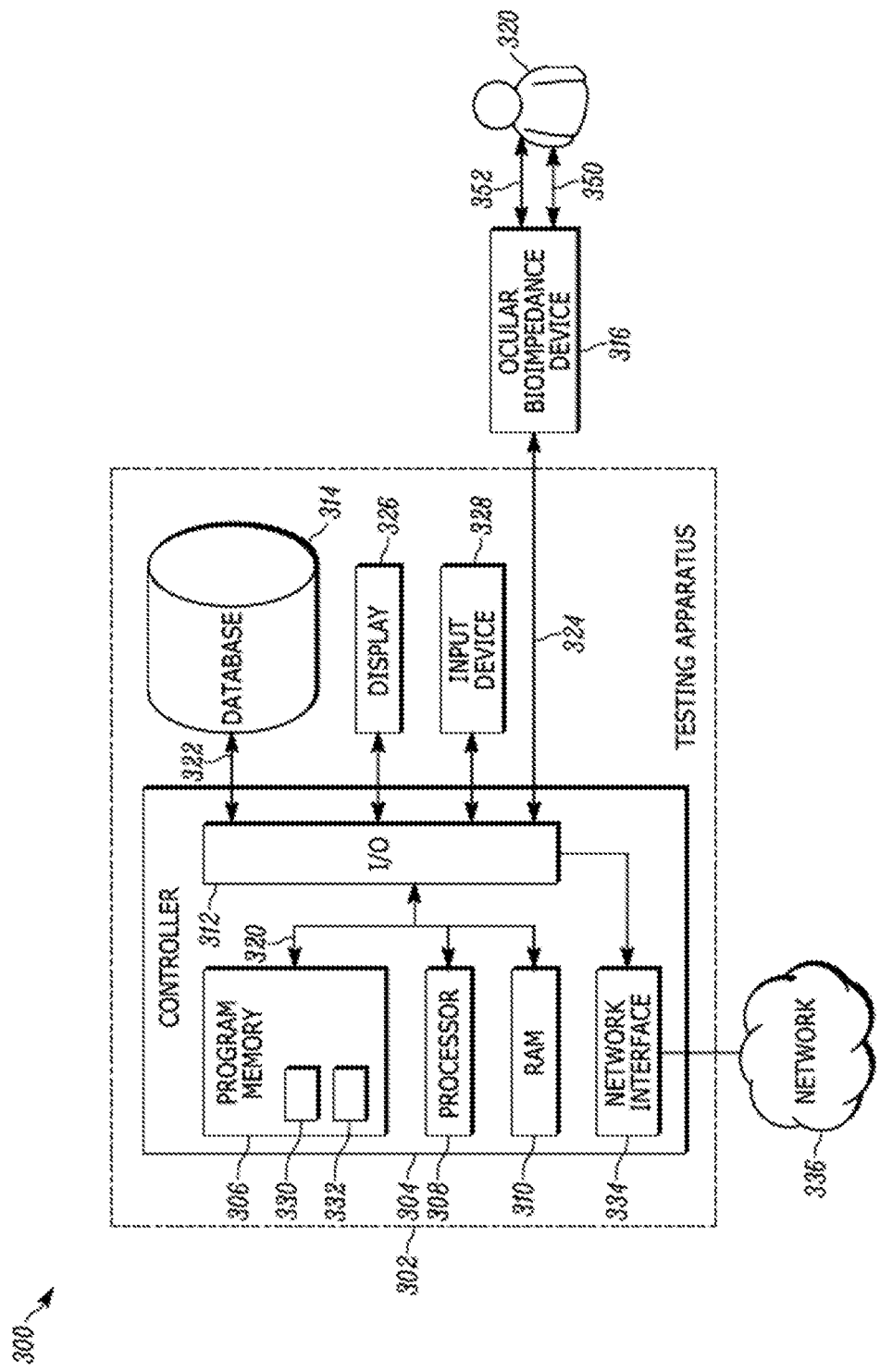
FIG. 10 illustrates an example ocular bioimpedance assessment system, in accordance with an example herein.
Figure 11:
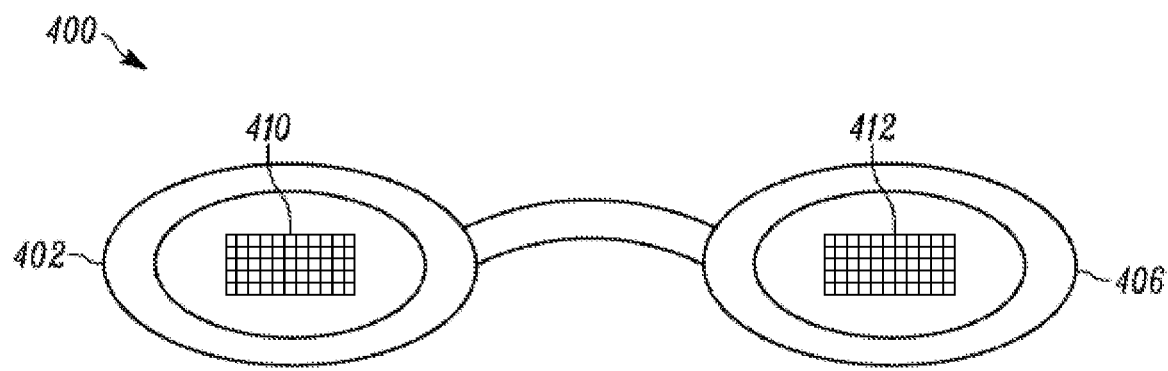
FIG. 11 illustrates an ocular bioimpedance measurement device, in accordance with another example.
Figure 12:
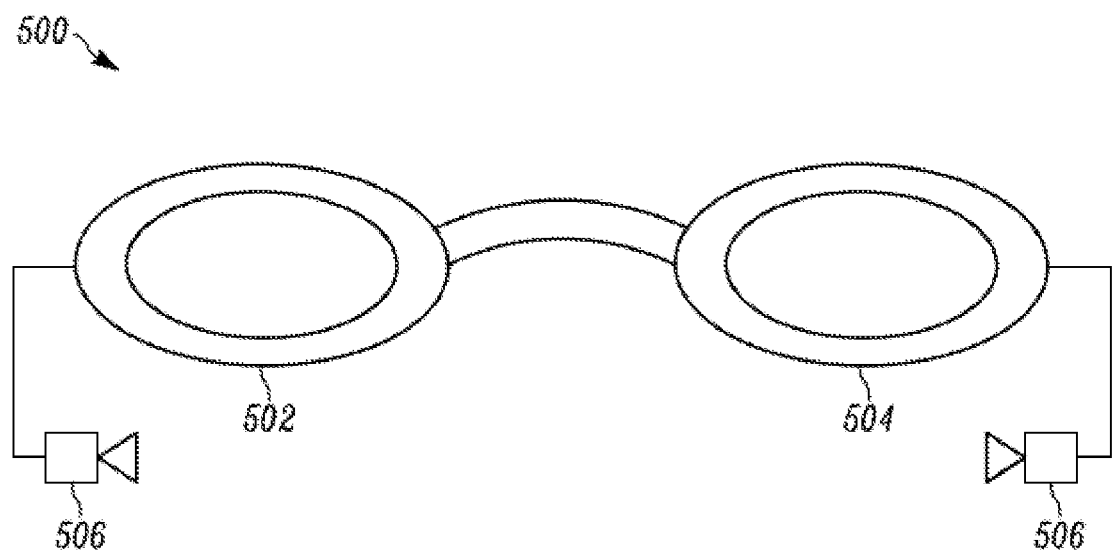
FIG. 12 illustrates an ocular bioimpedance measurement device, in accordance with another example.

Example devices are illustrated in FIGS. 11 and 12. FIG. 11 illustrates an ocular treatment device 400 having a lens 402 and a lens 406, each embedded with a photonic treatment LED array 410 and 412, respectively. The LED arrays 410 and 412 may be positioned over centralized portion of the cap forming the lens 402 and 406. These caps, as with the other example lens herein, may be opaque blocking external light from impinging upon the subject. Instead, for these examples, only photons from the arrays 410 and 412 would imping upon the subject. Of course, in other examples, the lens described herein may be transparent or semi-transparent (i.e., translucent). The arrays 410 and 412 generate photonic stimulation thereby providing therapy to the subject and/or diagnostic information to the subject, via this integrated goggle configuration. The device 400 may be controlled by a controller, an example of which is described in FIG. 10, that controls both photonic stimulation and electrical signals. The photonic stimulation may be provided during supply of an electrical signal applied and sensed through electrodes (not shown) that may be positioned at the lens rim for ocular region contact, as shown in the examples of FIGS. 8 and 9. The electrodes (not shown) would provide electrical signals for sensing bioimpedance and/or for treating the subject. In some examples, the photonic stimulation signals do not overlap with the supply of the electrical signal.

FIG. 12 illustrates a device 500 having lens 502 and 504 and integrated with an acoustic stimulation stage formed by two speakers 506 that are configured to provide acoustic stimulation for therapeutic or diagnostic purposes to the subject. While not limited to these examples, the speakers may be ear-plug styled headphones, over the ear headphones, miniature speakers attached to side of the subject or near the ocular region, including near or at a subject's temple, etc. That is, the speakers 506 may be configured to provide the acoustic stimulation at the ocular region and/or at a region on the subject other than the ocular region. Electrodes (not shown) would provide electrical signals for sensing bioimpedance and/or for treating the subject. A controller, like that of FIG. 10 would be used to control both electrical signals and acoustic stimulation signals.

FIG. 10 is an example block diagram 300 illustrating the various components used in implementing an example embodiment of the ocular bioimpedance measuring techniques herein. An analysis apparatus 302 is coupled to a patient 320 (e.g., a human or animal) via an ocular bioimpedance device 316 in accordance with executing the functions of the disclosed embodiments, and more specifically by current injecting electrodes 350 electrically coupled to the ocular region of the patient 320 and sensing electrodes 352 also electrically coupled to the ocular region of the patient 320. The analysis apparatus 302 may have a controller 304 operatively connected to the database 314 via a link 322 connected to an input/output (I/O) circuit 312. It should be noted that, while not shown, additional databases may be linked to the controller 304 in a known manner. The controller 304 includes a program memory 306, the processor 308 (may be called a microcontroller or a microprocessor), a random-access memory (RAM) 310, and the input/output (I/O) circuit 312, all of which are interconnected via an address/data bus 320. It should be appreciated that although only one microprocessor 308 is shown, the controller 304 may include multiple microprocessors 308. Similarly, the memory of the controller 304 may include multiple RAMs 310 and multiple program memories 306. Although the I/O circuit 312 is shown as a single block, it should be appreciated that the I/O circuit 312 may include a number of different types of I/O circuits. The RAM(s) 310 and the program memories 306 may be implemented as semiconductor memories, magnetically readable memories, and/or optically readable memories, for example. A link 324 may operatively connect the controller 304 to the ocular bioimpedance device 316 through the I/O circuit 312. The ocular bioimpedance device 316 is operatively connected to the patient 320 via electrodes 350 and 352.

The program memory 306 and/or the RAM 310 may store various applications (i.e., machine readable instructions) for execution by the microprocessor 308. For example, an operating system 330 may generally control the operation of the testing apparatus 302 and provide a user interface to the testing apparatus 302 to implement the processes described herein. The program memory 306 and/or the RAM 310 may also store a variety of subroutines 332 for accessing specific functions of the testing apparatus 302. By way of example, and without limitation, the subroutines 332 may include, among other things: a subroutine for providing electrical current to the ocular region, a subroutine for taking bioimpedance measurements with the ocular bioimpedance device 316, a subroutine for determining a brain health indicator such as MAP, ICP, CBF, CPP, and ocular-brain impedance, and other subroutines, for example, implementing software keyboard functionality, interfacing with other hardware in the analysis apparatus 302, etc. For example, the processes described hereinabove may be stored on the program memory 306 for execution by the processor 308. The program memory 306 and/or the RAM 310 may further store data related to the configuration and/or operation of the analysis apparatus 302, and/or related to the operation of one or more subroutines 252. For example, the data may be data gathered by the ocular bioimpedance device 316, data determined and/or calculated by the processor 308, etc. In addition to the controller 304, the analysis apparatus 302 may include other hardware resources. The analysis apparatus 302 may also include various types of input/output hardware such as a visual display 326 and input device(s) 328 (e.g., keypad, keyboard, etc.). In an embodiment, the display 326 is touch-sensitive, and may cooperate with a software keyboard routine as one of the software routines 332 to accept user input. It may be advantageous for the analysis apparatus 302 to communicate with a broader medical treatment network (not shown) through any of a number of known networking devices and techniques (e.g., through a commuter network such as a hospital or clinic intranet, the Internet, etc.). For example, the analysis apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system. By way of example, a network interface 334 is coupled to the I/O interface 312 for connecting the analysis apparatus 302 to a network 336, through a wired or wireless connection.

In this way, the system 300 may be configured to determine the bioimpedance of the patient and then further assess brain health, by determining, for example, whether the bioimpedance changes over time, changes in response to treatment, or changes based on some other conditions. The system 300 is configured to determine brain health indicators such as MAP, ICP, CBF, CPP, and/or ocular-brain impedance and measure the same over time. As discussed further, changes in brain impedance can be used to titrate specific therapies such as MAP, ventilation parameters, ICP (through removal of cerebral spinal fluid), blood and fluid transfusions in order to optimize CPP and preserve CAR to improve cerebral outcomes. For example decreases in brain impedance in response to a rising MAP (indicating abnormal CAR) may prompt health care providers to reduce MAP. Another example may include an increase in impedance with no change in MAP or current care may indicate a rise in ICP thus prompting therapies to reduce ICP.

Thus, in further example embodiments, the bioimpedance determination techniques herein are combined with treatment techniques to improve the efficacy of such treatments.

For example, transcranial direct current stimulation (tDCS) has been proposed as a neuromodulation technique in the treatment of psychiatric illnesses, such as depression or schizophrenia, as well as in providing cognitive enhancement, such as memory enhancement, executive function enhancement, attention enhancement, and fluency enhancement. The techniques can include applying direct current stimulation to the brain through the use of electrodes externally placed on the skin at various locations on the scalp. However, the amount of current that actually penetrates the scalp and flows into the brain is believed to be very small. By including, through the techniques herein, electrodes in the ocular region it is now possible to deliver higher levels of current to the brain as outlined in the previously described experiments where ocular versus scalp pathways were compared in their ability to penetrate into the brain. This ocular pathway for delivery of direct current may be coupled with the simultaneous or intermittent measuring of brain bioimpedance in accordance with the present techniques as a means to help monitor therapy, as desired. This bioimpedance-based feedback can then be used to further guide the treatment, either manually or through completely- or partially-automated computer processing of the treatment signal. For example, in the context of determining an enhanced PRx using the present techniques, the transcranial direct current stimulation controller that controls the electrical stimulation signals sent to the brain can be configured to automatically re-adjust the electrical signals (i.e., current value, frequency, waveform, voltage, etc.) in response to changes in the enhanced PRx, e.g., from the PRx changing from a negative value to a positive value.

In some example embodiments, traditional tDCS using the scalp as the site of current injection may be directed by using the ocular-brain bioimpedance signal to optimize the location of the tDCS electrodes. For example, tDCS electrodes may be positioned on a subject and a treatment is commenced. The bioimpedance is measured; and the electrodes are placed at another location, from which the bioimpedance is re-measured. By assessing the bioimpedance at each location, or a brain health indicator determined from the bioimpedance at each location, a treatment professional can determine which tDCS electrode location is better for treating the subject, for example, which location results in the better brain health indicator value.

These ocular-brain region bioimpedance enhanced treatment techniques are not limited to tDCS. The techniques can be used in a similar manner with transcranial alternating current stimulation (tACS) to control stimulation signal characteristics, the location of the tACS stimulation electrodes, etc. tACS is used similar to tDCS for numerous neuro- and neuro-psychiatric conditions ranging from stroke to depression. Thus the ocular-brain pathway techniques herein may be used to both deliver tACS and/or tDCS as well as monitor brain bioimpedance in addition to the ocular-brain pathway of bioimpedance being used to optimize scalp electrode placement for tDCS and tACS.

In yet other examples, these ocular-brain bioimpedance enhanced treatments may include biophotonic-based treatments and acoustic-based treatments. Biophotonic treatments include proton photonic stimulation to a subject and monitoring the effects thereof. These biophotonic treatments include what is commonly referred to as red light therapy, blue light therapy, infrared therapy, where stimulation photons are provided through the vision system of a subject. The bioimpedance techniques described herein may be used to monitor the effectiveness of biophotonic therapy by measuring, for example, a brain health indicator during treatment and assessing the effectiveness of that treatment in response.

Acoustic-based treatments may be analyzed in a similar manner. In some examples, acoustic energy is applied to the head of a subject to detect increases in intracranial pressure. Acoustic eye patches, for example, are applied to a patient's eye or eyelid, and an ultrasonic sweep generator applies an acoustic signal across the patient's skull, the signal being swept across a predetermined range. The eye patches have piezoelectric film sensors for measuring the acoustic signal. In one embodiment the predetermined range is in the ultrasonic band and an analyzer determines from the output of the sensors a resonant frequency and a damping of acoustic amplitude at said resonant frequency, there being a correlation between said damping and intra cranial pressure. In another embodiment the predetermined range includes a range less than 20 kHz and the analyzer determines retinal artery pulsations, with pressure being applied to the eye until the pulsations disappear, such pressure being a measure of intra cranial pressure. These acoustic eye patches are configured with bioimpedance electrodes that measure the ocular-brain region bioimpedance of the subject during application of the acoustic signal. The effectiveness of the acoustic signals may then be assessed based on the changes in the bioimpedance values or brain health indicator(s) derived therefrom. And, as is the case with the other treatment examples herein (tDCS, tACS, biophotonics, etc.), the treatment signals may be adjusted to improve brain health based on the measured bioimpedance response.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or that are permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or by processor-implemented hardware modules. The performance of certain of the operations may be distributed among the one or more processors, not only residing within a single machine (having different processing abilities), but also deployed across a number of machines. In some example embodiments, the processors may be located in a single location (e.g., deployed in the field, in an office environment, or as part of a server farm), while in other embodiments the processors may be distributed across a number of locations.

Unless specifically stated otherwise, discussions herein using words such as "processing," "computing," "calculating," "determining," "presenting," "displaying," or the like may refer to actions or processes on a GPU thread that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. An apparatus for evaluating brain health of a subject, the apparatus comprising:
   one or more electrodes;
   one or more processors; and
   a computer-readable memory storing non-transient instructions that when executed by the one or more processors cause the apparatus to:
      provide, using the one or more electrodes, electrical current through an optical nerve to a brain of the subject via an ocular region of the subject;
      sense, using the one or more electrodes, an electrical signal obtained from the ocular region of the subject;
      determine a bioimpedance value of the subject from the electrical signal, wherein the bioimpedance value represents a bioimpedance for a conduction path that includes at least a portion of the ocular and brain regions of the subject; and
      determine a brain health indicator from the bioimpedance value.

2. The apparatus of claim 1, wherein the brain health indicator indicates at least one of changes (i) in cerebral blood volume (CBV), (ii) cerebral autoregulation (CAR), (iii) intracranial pressure (ICP), (iv) cerebral perfusion pressure (CPP), (v) a perfusion reactivity index (PRx), (vi) cerebral blood flow (CBF), (vii) blood pressure, and (viii) ventilation.

3. The apparatus of claim 1, wherein the computer-readable memory storing non-transient instructions that when executed by the one or more processors cause the apparatus to determine respiration rate, respiration quality, and/or heart rate of the subject.

4. The apparatus of claim 1, further comprising a goggle having a first lens and a second lens, wherein the one or more electrodes are positioned on interior surfaces of the first and second lens, respectively, to provide electrical conduction path from the ocular region of the subject to the brain.

5. The apparatus of claim 4, wherein the first lens comprises current injecting electrodes and the second lens comprises current sensing electrodes.

6. The apparatus of claim 4, wherein the first lens comprises current injecting electrodes and current sensing electrodes, and wherein the second lens comprises current injecting electrodes and current sensing electrodes.

* * * * *